(12) United States Patent  (10) Patent No.: US 8,474,067 B2
Reimer                    (45) Date of Patent:     Jul. 2, 2013

(54) SPINAL PROTECTIVE DEVICE

(76) Inventor: Milton D. Reimer, Sanford (CA)

( * ) Notice: Subject to any disclaimer, the term of this patent is extended or adjusted under 35 U.S.C. 154(b) by 347 days.

(21) Appl. No.: 12/954,788

(22) Filed: Nov. 26, 2010

(65) Prior Publication Data

US 2012/0131736 A1    May 31, 2012

(51) Int. Cl.
    *A41D 13/00* (2006.01)
(52) U.S. Cl.
    USPC .................................. 2/467; 602/19
(58) Field of Classification Search
    USPC ............... 128/846; 2/455, 467, 468; 602/19
    See application file for complete search history.

(56) References Cited

U.S. PATENT DOCUMENTS

| 5,328,447 | A | 7/1994 | Kapounek et al. |
| 5,586,561 | A | 12/1996 | Archer, III |
| 5,855,561 | A | 1/1999 | Glidden |
| 6,687,920 | B2 | 2/2004 | Berns |
| 6,852,087 | B1 * | 2/2005 | Dainese .......................... 602/19 |
| 7,329,230 | B2 | 2/2008 | Mazzarolo |
| 2010/0122404 | A1 * | 5/2010 | Bowlus et al. ..................... 2/467 |
| 2010/0263111 | A1 | 10/2010 | Leatt et al. |

FOREIGN PATENT DOCUMENTS

| DE | 19527036 | 1/1997 |
| GB | 2345435 | 7/2000 |
| WO | 9718723 | 5/1997 |
| WO | 2011091981 | 8/2011 |

* cited by examiner

*Primary Examiner* — Katherine Moran
(74) *Attorney, Agent, or Firm* — Ryan W. Dupuis; Kyle R. Satterthwaite; Ade & Company Inc.

(57) ABSTRACT

A spinal protective device includes a plurality of support members abutted in series with one another along a spine of a user. Each adjacent pair of support members has a respective pair of forward fulcrum contact areas where the support members abut one another for relative pivotal movement in a hyperflexion direction and a respective pair of rearward fulcrum contact areas where the support members abut one another for relative pivotal movement in a hyperextension direction. A rear tension member connected between the support members limits relative movement in the hyperflexion direction and a front tension member connected between the support members limits relative movement between the support members in the hyperextension direction. Straps about the torso secure the support members along the spine of the user.

19 Claims, 6 Drawing Sheets

SPINAL PROTECTIVE DEVICE

FIELD OF THE INVENTION

The present invention relates to a spinal protective device for being supported along the spine of a user for limiting movement of the spine in the hyperflexion direction, and more particularly the present invention relates to a spinal protective device which limits movement of the spine in both the hyperflexion and the hyperextension directions.

BACKGROUND

Spinal injuries are common in many sports including motocross, snowmobiling, skateboarding, and other sports generally referred to as extreme sports for example. Often spinal injuries result in permanent damage so many efforts are made to protect the user from such injuries.

The following U.S. Pat. No. 6,687,920 by Berns; U.S. Pat. No. 5,855,561 by Glidden; U.S. Pat. No. 6,852,087 by Dainese; U.S. Pat. No. 5,328,447 by Kapounek et al; and U.S. Pat. No. 7,329,230 by Mazzarolo; and Published Application 2010/0122404 by Bowlus et al disclose various devices related to spinal protection. These prior art devices generally require a complex arrangement of supporting elements which are connected to one another by hinges or other complex formed parts which are costly and difficult to manufacture and assemble. Furthermore, the strength of the assembled device relies on the cooperation of many individual parts which increases the potential for failure and decreases the effective protection provided.

SUMMARY OF THE INVENTION

According to one aspect of the invention there is provided a spinal protective device comprising:

a plurality of support members arranged to be abutted in series with one another in a longitudinal direction so as to extend longitudinally along a spine of a user;

each support member including a supportive inner surface at a front side of the support member which spans in a lateral direction so as to be arranged to extend laterally across a back of the user;

each adjacent pair of support members further comprising a respective pair of forward fulcrum contact areas where the support members abut one another for relative pivotal movement in a hyperflexion direction about a forward lateral axis; and a rear tension member arranged to be connected under tension between the support members at a location spaced rearwardly from the forward fulcrum contact areas so as to be arranged to limit relative movement between the support members in the hyperflexion direction; and a plurality of straps arranged to be extended about a torso of a user so as to secure the support members extending longitudinally along the spine of the user.

By providing support members which are abutted with one another to define respective fulcrum contact areas therebetween joined by a tension member spaced from the fulcrum contact areas, a very simple construction results which only relies on the tension member for strength so as to reduce the large potential for failure of prior art configurations. Furthermore, the resulting simplified construction is of lower cost and is easier to assemble than prior art spinal protective devices. By providing a horizontal space between the tension member and the cooperating fulcrum contact areas, a high resistance to bending moments is provided so that the device according to the present invention is very strong while also allowing relatively free movement within the acceptable range of flexing or extension before the limit of movement prescribed by the tension member is reached.

Preferably the rear tension member comprises a single, integral and flexible member spanning all of the support members and which is adjustable in length.

Each support member may comprise a forward portion generally comprising a plate spanning in the lateral direction to define the inner surface arranged to engage the user and a rearward portion comprising a lobe projecting rearwardly outwardly from the forward portion at a central location thereon and which defines the fulcrum contact areas thereon.

The inner surfaces of adjacent support members are preferably supported relative to the fulcrum contact areas so as to be arranged to remain spaced apart from one another in the longitudinal direction when the support members are pivoted relative to one another in the hyperflexion direction to a hyperflexion limit prescribed by the rear tension member.

The forward fulcrum contact areas are spaced rearwardly from the inner surfaces of the respective support members.

The straps preferably include a mid-torso strap coupled at opposing ends to opposing sides of a central one of the support members so as to be arranged to extend about the torso of the user at a thoracic region; a pair of shoulder straps, each anchored to an uppermost one of the support members at one end and anchored to the mid-torso strap at an opposing end; a waist strap coupled at opposing ends to opposing sides of a lowermost one of the support members so as to be arranged to extend about a waist of the user; and a pair of leg straps secured at opposing ends to the lowermost one of the support members so as to be arranged to extend about respective legs of the user.

Preferably each adjacent pair of support member further comprises a respective pair of rearward fulcrum contact areas where the support members abut one another for relative pivotal movement in a hyperextension direction about a rearward lateral axis. In this instance a front tension member is arranged to be connected under tension between the support members at a location spaced forwardly from the rearward fulcrum contact areas so as to be arranged to limit relative movement between the support members in the hyperextension direction.

Preferably the front tension member and the rear tension member are independently adjustable in length.

The forward fulcrum contact areas are preferably spaced forwardly towards the inner surfaces of the support members in relation to the corresponding rearward fulcrum contact areas.

The tension members are located between the forward and rearward fulcrum contact areas.

The fulcrum contact areas and the tension members are preferably aligned in a generally common vertical plane oriented perpendicularly to the lateral direction.

Each support member of each adjacent pair of support members preferably includes an end face oriented transversely to the rear tension member in abutment with the end face of the other support member of the adjacent pair of support members in which the end faces locate the forward and rearward fulcrum contact areas thereon.

The support members are preferably only connected by the mating abutment of respective ends with one another and the tension members connected between the support members.

The support members preferably include an uppermost support member at a top end, a lowermost support member at a bottom end and at least one intermediate support member between the uppermost and lowermost support members in which the front and rear tension members are anchored at opposing ends on the uppermost and lowermost support members respectively and extend through said at least one intermediate support member.

The rear tension member is preferably received through respective bores extending in the longitudinal direction through respective ones of the support members, the bores being elongate in the lateral direction.

Preferably one of the support members of each adjacent pair comprises a protrusion and the other one of the support members of the adjacent pair comprises a socket arranged to receive the protrusion therein between the respective forward and rearward fulcrum contact areas of the support members.

The protrusion is preferably arranged to mate with the socket such that the respective support members are pivotal relative to one another about a longitudinally extending axis within a prescribed range of a degrees, for example limited to a range of a few degrees in either direction from a normal use centered position.

According to one embodiment, when the tension members extend through the support members through respective bores, the bores are located in the protrusion and the socket respectively.

Alternatively, the protrusion and the socket are located between the front tension member and the rear tension member.

When each adjacent pair of support member abuts one another at respective ends faces, preferably each end face further comprises a first lateral fulcrum and a second lateral fulcrum spaced apart in laterally opposed directions from the rear tension member. In this instance each adjacent pair of support members are preferably arranged to abut one another at the first lateral fulcrums respectively for relative pivotal movement in a first lateral direction up to a first lateral limit when the rear tension member is under tension. Similarly, each adjacent pair of support members are preferably arranged to abut one another at the second lateral fulcrums respectively for relative pivotal movement in a second lateral direction up to a second lateral limit when the rear tension member is under tension.

Preferably the first and second lateral fulcrums are substantially centered between the front and rear tensions members in a direction of a transverse axis extending between the front and rear tensions members.

Preferably the spinal protective device is provided in combination with a neck protective device. In some embodiments, the neck protective device is a separate device which preferably comprises a pair of shoulder portions arranged to extend over respective shoulders of a user, a rear collar portion joined between the shoulder portions and extending upwardly therefrom so as to be arranged to limit rearward movement of a head of the user, and a depending portion arranged to extending downwardly from the rear collar portion along a back of the user, wherein an uppermost one of the support members includes a channel at a rear side of the support member arranged to receive the depending portion of the neck protective device therein.

In alternative embodiments, the spinal protective device incorporates a neck protective device integrally therewith. In this instance the spinal protective device preferably includes a pair of shoulder portions integrally formed with an uppermost one of the support members which are arranged to extend over respective shoulders of the user and a rear collar portion integrally formed with the uppermost one of the support members to extend upwardly therefrom above the shoulder portions so as to be arranged to limit rearward movement of a head of the user.

Some embodiments of the invention will now be described in conjunction with the accompanying drawings in which:

BRIEF DESCRIPTION OF THE DRAWINGS

In the drawings like characters of reference indicate corresponding parts in the different figures.

DETAILED DESCRIPTION

Figure 1:
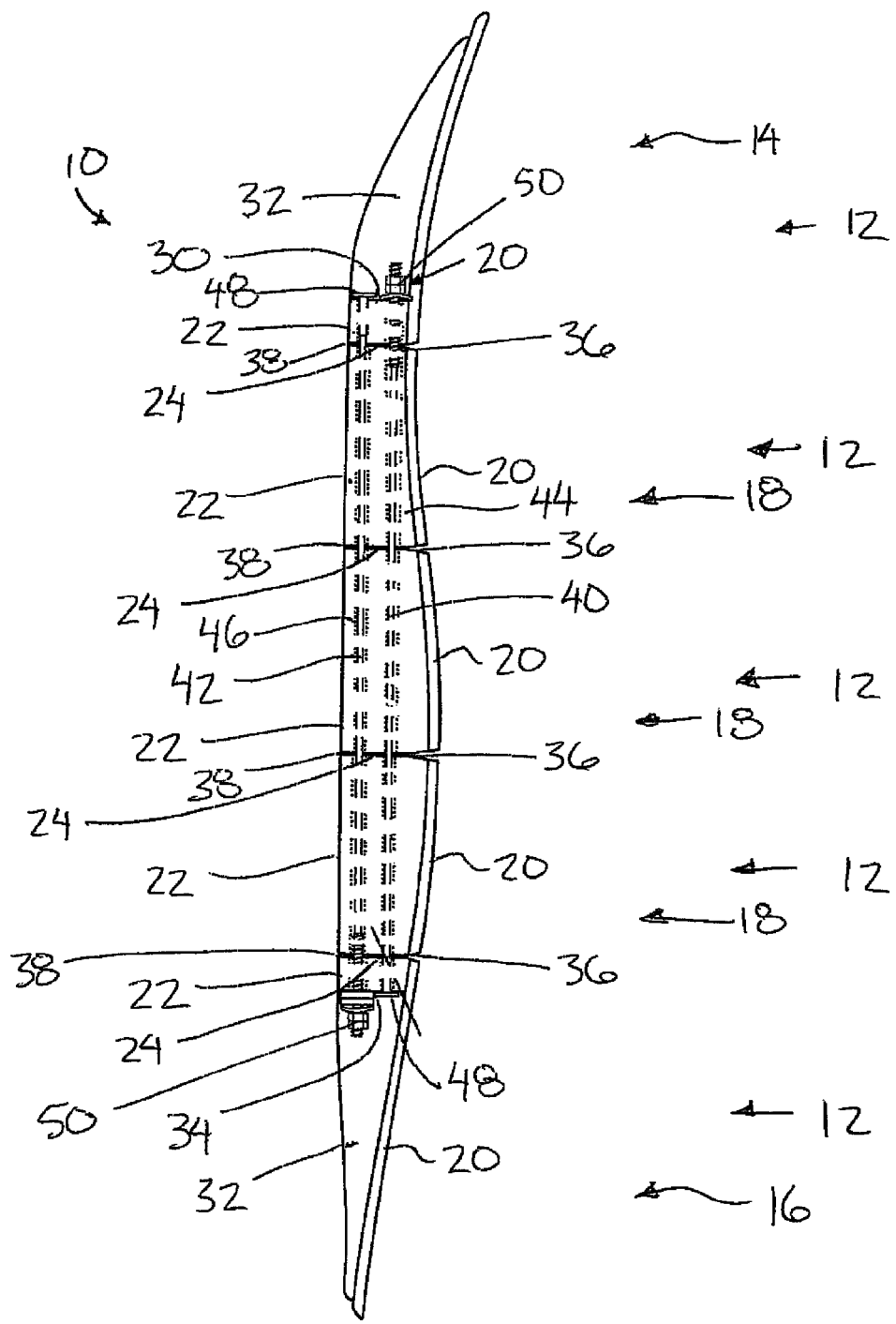
FIG. 1 is a side elevational view of the spinal protective device according to a first embodiment.

Referring to the accompanying figures there is illustrated a spinal protective device generally indicated by reference numeral 10. The device 10 is particularly suited for support along the spine of a user to limit the range of movement in the hyperflexion and hyperextension directions. Although various embodiments are described and illustrated herein, the common features of the various embodiments will first be described.

The device 10 in each instance comprises a plurality of support members 12 which are abutted in series with one another in a longitudinal direction so as to be arranged to extend in the longitudinal direction along the spine of the back of a user. In the illustrated embodiment five support members 12 are provided such that the support members include an uppermost member 14, a lowermost member 16, and three intermediate members 18 between the uppermost and lowermost members. The uppermost member 14 is arranged to be located adjacent the cervical region of the spine while the lowermost member 16 is arranged to be located adjacent the lumbar region of the user. The three intermediate members 18 thus substantially span the thoracic region of the spine.

Each support member 12 includes a forward portion 20 generally comprising a plate of substantially constant thickness for defining an inner surface of the member which engages the user and which spans at least part-way or most of the way across the back of the user in the lateral direction. The inner surface conforms to the shape of the back of the user by being slightly concave in the lateral direction. The intermediate members adjacent the lower thoracic region are generally concave in the longitudinal direction while the intermediate member 18 at the upper end of the thoracic region is generally concave in the longitudinal direction to conform to the typical curvature of a user's spine.

Each of the plates becomes somewhat narrower in height from a center to each of the laterally opposed outer side edges such that when the members are abutted end to end at a central location, the support members are free to pivot relative to one another in a generally lateral direction while the central portions of the members remain substantially abutted with one another.

The uppermost support member is also somewhat concave in the longitudinal direction to follow the contour of the lower cervical region. The uppermost support member 14 is also longer in the longitudinal direction than the intermediate members.

The lowermost member is also longer in the longitudinal direction than the intermediate members, but is generally flat in the longitudinal direction for accommodating a flatter portion of the spine near the upper lumbar and lower thoracic region.

Each support member further includes a rearward portion 22 in the form of a lobe on the rear of the plate forming the forward portion. The rearward portion projects rearwardly out of the plane of the plate forming the forward portion at a location laterally centered thereon between laterally opposed side edges. The rearward portion is formed integrally, seamlessly and continuously with the body of the forward portion so as to be formed of like material throughout.

For each of the intermediate members 18 the rearward portion 22 spans the full height in the longitudinal direction of the support member. Both the top and bottom ends define a generally flat end face 24 which is substantially perpendicular to the longitudinal direction and which is suited for abutment against the corresponding end face of an adjacent one of the support members.

At the top end, the end face locates a socket 26 recessed downwardly therein at a central location along a lateral axis as well as being centered along a transverse axis oriented perpendicularly to the lateral axis in a forward to rearward direction. At the bottom end, a protrusion 28 extends outwardly in the longitudinal direction beyond the end face for being received in the socket 26 of the support member therebelow.

The uppermost support member 14 includes a rear portion in which the bottom end defines an end face 24 perpendicular to the longitudinal direction in alignment with the bottom end of the support member for engagement with the corresponding end face of the intermediate member therebelow. The rear portion of the uppermost member also includes a top face 30 parallel to the bottom end face in relatively close proximity to the bottom end face such that the rear portion only spans a small portion of the overall height of the support member in the longitudinal direction at a location nearest to the bottom end of the support member.

Two parallel and spaced apart ribs 32 are connected to laterally opposed sides of the rear portion to extend upward in the longitudinal direction therefrom along the rear surface of the forward portion 20 of the uppermost member to provide added structural support to the rear portion 22 at the bottom end of the support member. The ribs 32 are reduced in thickness relative to the forward portion as the ribs extend upwardly to the top end of the uppermost support member. The uppermost member further includes a protrusion 28 formed on the bottom end face 4 which extends downward for engagement into the socket of the intermediate member therebelow.

The lowermost support member includes a rear portion 22 which is substantially opposite to the rear portion of the uppermost member. The rearward portion 22 of the lowermost member includes a top end face 24 which is perpendicular to the longitudinal direction in alignment with the top end of the support member which locates a socket 26 centrally therein for receiving a corresponding protrusion 28 of the intermediate member thereabove therein. The bottom face 34 of the rear portion of the lowermost support member is parallel to the top end face 24 at a location spaced therebelow such that the rear portion also only spans a small portion of the overall height of the lower support member in the longitudinal direction at a location nearest to the top edge of the lowermost support member. Two support ribs 32 are also provided at parallel and spaced apart locations at opposing sides of the rear portion 22 of the lowermost support member to extend downwardly therefrom along the rear surface of the forward portion 20 to provide added structural support to the rear portion 22. The ribs 32 on the lowermost support member also are reduced in thickness relative to the forward portion with increasing distance from the rear portion 22 to which they are connected.

At the abutment between each adjacent pair of the support members 12 a protrusion on one of the members is received within a mating socket on the other member such that the socket and protrusion pair have a substantially mating profile. The socket is slightly larger in dimension than the protrusion in each instance to allow some small relative pivotal movement or relative rotation between the two adjacent and abutted support members about a vertical longitudinal axis through a range of a few degrees in each direction from a central aligned position. The non-circular cross section of the socket and protrusion prevents relative rotation beyond the few degrees provided by the larger socket.

Each adjacent pair of the series of support members has a respective pair of forward contact areas defining forward fulcrums 36 and a respective pair of rearward contact areas which function as rearward fulcrums 38 when abutted with one another. Accordingly each end face includes one forward fulcrum so that the pair of forward fulcrums are abutted when the end faces of the adjacent pair of support members are abutted. Similarly each end face includes one rearward fulcrum so that the pair of rearward fulcrums are abutted when the end faces of the adjacent pair of support members are abutted.

In this instance, each end face 24 which abuts an adjacent member has a respective forward fulcrum 36 at a location which is laterally centered and forward of the corresponding socket or protrusion as well as a rearward fulcrum 38 which is also laterally centered but at the rear side of the support member so as to be located rearward of the corresponding socket or protrusion. The abutment of two forward fulcrums between an adjacent pair of support members thus defines a forward lateral axis about which the support members are pivotal relative to one another in a hyper-flexion direction. Similarly, the abutment of two rearward fulcrums 38 between an adjacent abutted pair of support members effectively defines a rearward lateral axis spaced rearward of the forward axis about which the support members are pivotal relative to one another in a hyperextension direction. The forward fulcrum 36 is near to but spaced rearwardly from the inner surface of the forward portion of each respective support member.

A front tension member 40 and a rear tension member 42 are provided such that each spans across all of the support members in connection therewith to maintain the support members abutted with one another in series in a longitudinal direction. Each tension member comprises a steel cable which is adjustable in length and which is anchored at opposing ends on the uppermost and lowermost support members respectively such that the tension members span fully through each of the intermediate members therebetween. The forward tension member serves to limit relative movement between the support members in the hyperextension direction while the rear tension member 42 limits relative pivotal movement in the hyperflexion direction.

Bores are provided in the rearward portions 22 of each support member for receiving the tension members extending in the longitudinal direction therethrough. More particularly each support member includes a front bore 44 extending fully through the support member between the opposing end faces for receiving the front tension member at a location which is near to the forward fulcrum 36. Similarly each support member includes a rear bore 46 extending fully therethrough between the opposing end faces to receive the rear tension member therethrough at a location near the rear fulcrum.

The bores are located in alignment along the transverse axis extending between the respective forward and rearward fulcrums such that the bores are located at an intermediate location between the fulcrums. The bores have a diameter along the transverse axis which is near to the dimension of the cable so as to allow minimal relative movement along the transverse axis; however the bores have a larger diameter so as to be elongate in the lateral direction. The greater dimension of the bores in the lateral direction than the tension members allows some relative rotation between adjacent abutted support members through a range of a few degrees in either direction from a centred aligned position about the vertical longitudinal axis.

Each of the tension members includes an end flange 48 fixed at one end thereof which is increased in diameter for abutment against a corresponding external end face of the uppermost or lowermost support member. The tension member is then inserted through all of the bores in all of the support members with the opposing end being threaded for receiving a nut 50 threaded thereon. The larger diameter of the threaded nut 50 serves to abut the external end face of the opposing uppermost or lowermost support member for clamping the support members between the nut 50 and the end flange 48 of each support member.

By varying the amount the nut is threaded onto the support member the effective length of the support member between the flange 48 and the nut 50 can be adjusted which effectively adjusts the clamping force or tension applied by the tension member to the support members clamped together. The tension members are mounted such that the nut of one of the tension members is located at the top face of the uppermost member while the threaded nut of the other tension member is located at the bottom face of the lowermost support member so that the adjustment of the nuts can be easily performed independently of one another and without interference of one another.

Adjusting the length of the rear tension member 42 effectively adjusts the setting of a prescribed limit of hyperflexion movement between adjacent support members about the forward axes defined by the respective forward fulcrums. The forward portions 20 defining the inner face of each support member are arranged to be shorter in the longitudinal direction than the rear portions 22 such that at the hyperflexion limit a gap is maintained between the inner surfaces of each adjacent pair of support members for comfort of the user and to prevent pinching.

Similarly the front tension member 40 is used to adjust the setting of a prescribed limit of hyperextension movement between adjacent support members about respective rearward axes defined by the rearward fulcrums respectively.

Each end face 24 of each support member of each abutted pair of the support members also has a first lateral contact area 64 and a second lateral contact area 66. The first and second lateral contact areas of each end face 24 are offset in the lateral direction in opposing directions from the transverse axis extending between the front and rear tension members such that the front and rear tension members are substantially centered in the lateral direction relative to the lateral contact areas. Also, each of the lateral contact areas is arranged to be substantially centered in the direction of the transverse axis 68.

The function of the first and second lateral contact areas is to limit the amount of relative pivotal movement between the support members in respective first and second lateral directions. More particularly, at each abutted pair of end faces, the respective pair of first lateral contact areas 64 are arranged to abut one another to define first lateral fulcrums in contact with one another that limit relative pivotal movement between the abutted support members in a first lateral direction about a first axis extending through the first lateral fulcrums in the direction of the transverse axis 68 when both front and rear tension members are under a substantially even amount of tension. The front and rear tension members are under tension with the first lateral fulcrums in abutment with one another at a prescribed first lateral limit of the relative movement of the support members in the first lateral direction.

Similarly, the respective pair of second lateral contact areas 66 are arranged to abut one another to define second lateral fulcrums in contact with one another that limit relative pivotal movement between the abutted support members in a second lateral direction about a second axis extending through the second lateral fulcrums in the direction of the transverse axis 68 when both front and rear tension members are under a substantially even amount of tension. The front and rear tension members are under tension with the second lateral fulcrums in abutment with one another at a prescribed second lateral limit of the relative movement of the support members in the second lateral direction.

The resulting construction is simple and easy to manufacture and assemble as only the two cables defining the forward and rearward tension members are used to hold all of the support members in mating abutment with one another at the respective end faces thereof with the mating socket and protrusions serving primarily to maintain alignment.

The relatively loose fit between each socket and protrusion pair as well as the shape and size of the bores relative to the tension members received therethrough allows some twisting movement of the support members relative to one another about the longitudinal axis. Furthermore, the height of the plates forming the forward portions which narrow in the lateral direction allow some side to side flexing so as to not limit desirable mobility of the user.

The tension members are also set to be relatively loose in a relaxed neutral position of the device 10 so that forward flexing in the flexion direction and rearward extension in the extension direction are not limited within the range of acceptable movement until the respective hyperflexion limit and hyperextension limits are reached. Similarly free movement is allowed in both first and second lateral directions until the respective first and second lateral limits are reached.

The bores receiving the tension members, the socket protrusion pairs, and the forward and rearward fulcrums are all arranged to be aligned in a generally common vertical plane oriented in the transverse direction perpendicularly to the lateral direction. Accordingly considerable strength is provided to resist the forward and rearward flexing beyond the hyperextension and hyperflexion limits.

A plurality of straps are used to secure the device 10 to the body of the user. In particular a mid-torso strap 52 is anchored at opposing ends on opposing sides of the central one of the intermediate members so as to extend about the torso of the user at the thoracic region. Two shoulder straps 54 are also provided which are each anchored at one end to a respective side of the uppermost support member with the opposing end of the strap being integrally formed with a respective end of the mid-torso strap 52. Accordingly tightening the mid-torso strap across the chest of the user effectively tightens the shoulder strap about the respective shoulder of the user.

The straps also include a waist strap 56 anchored at opposing ends on opposing sides of the lowermost support member for extending about the waist of the user. The straps further comprise a pair of leg straps 58 each anchored at a first end at a central location at a bottom end of the lowermost support member while being anchored at the opposing end to a respective side of the lowermost support member. Each leg strap is thus suited for wrapping about a respective leg of the user.

A chest pad 60 is connected to the mid-torso strap 52 so that the user is arranged to be strapped between the chest pad 60 at the chest area and the protective device 10 at the back area. The chest pad distributes the load of the mid-torso strap 52 across the chest of the user primarily in the instances of a severe hyperextension load. The shoulder straps also include a pad section 62 which is padded or formed to be wider for distributing the force in the region extending over each shoulder. Other pad can be similarly provided on the other straps for distributing load across appropriate body surfaces of the user.

Figure 5:
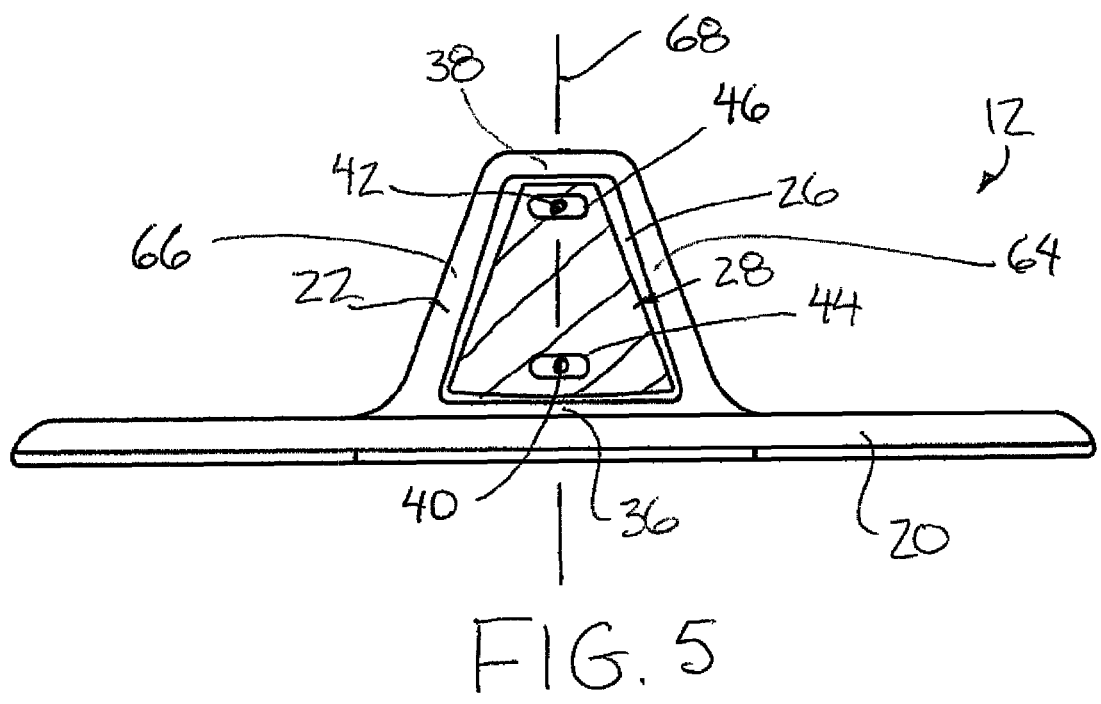
FIG. 5 is an end view along the line 5-5 of the spinal protective device according to FIG. 1.

As shown in the first embodiment of FIG. 5, a cross section of each protrusion and corresponding socket in this instance may be generally trapezoidal which serves to limit the relative rotation about the longitudinal axis between two abutted support members beyond a few degrees in each direction from the central neutral position. The forward and rearward bores receiving the front and rear tension members in this instance are aligned with the protrusions and sockets respectively so that the bores extend through the protrusions in alignment with the respective sockets at spaced apart positions along the transverse axis.

Figure 6:
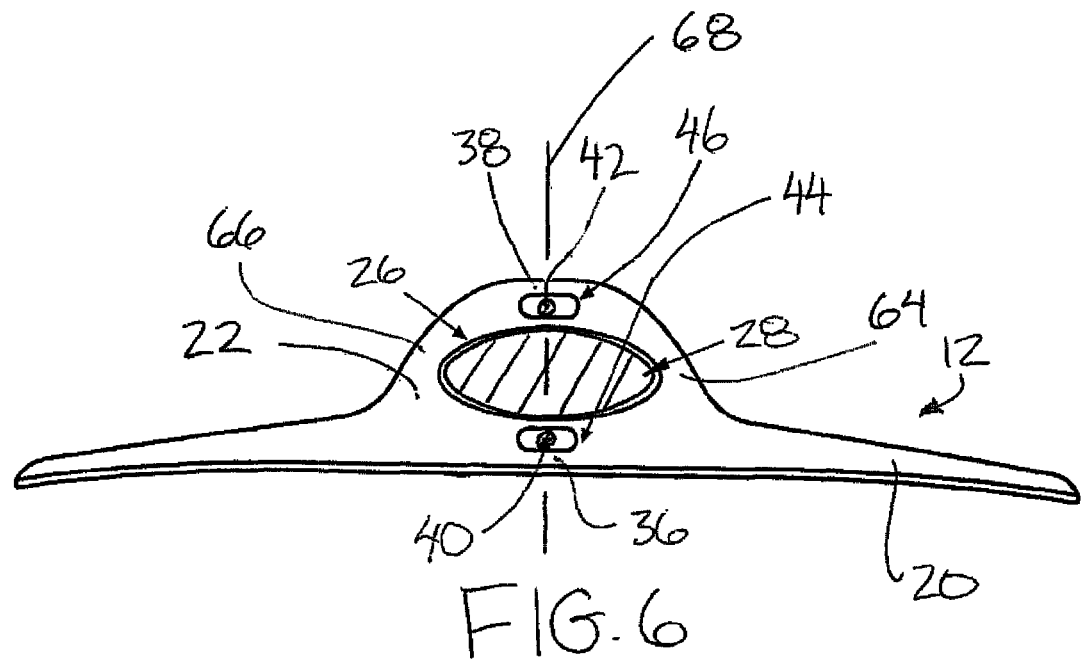
FIG. 6 is an end view similar to FIG. 5 of an alternative embodiment of the spinal protective device.

Turning now to the alternative embodiment shown in FIG. 6, the socket and corresponding protrusion of each socket and protrusion pair in this instance are shown to be generally oval in shape so as to be more elongate in the lateral direction. The socket and protrusion pair in each instance is also located at a central location between the front bore receiving the front tension member and the rear bore receiving the rear tension member. The oval shape in this instance also resists relative rotation about the longitudinal axis between two abutted support members beyond the range of a few degrees in each direction from a central neutral position.

Figure 2:
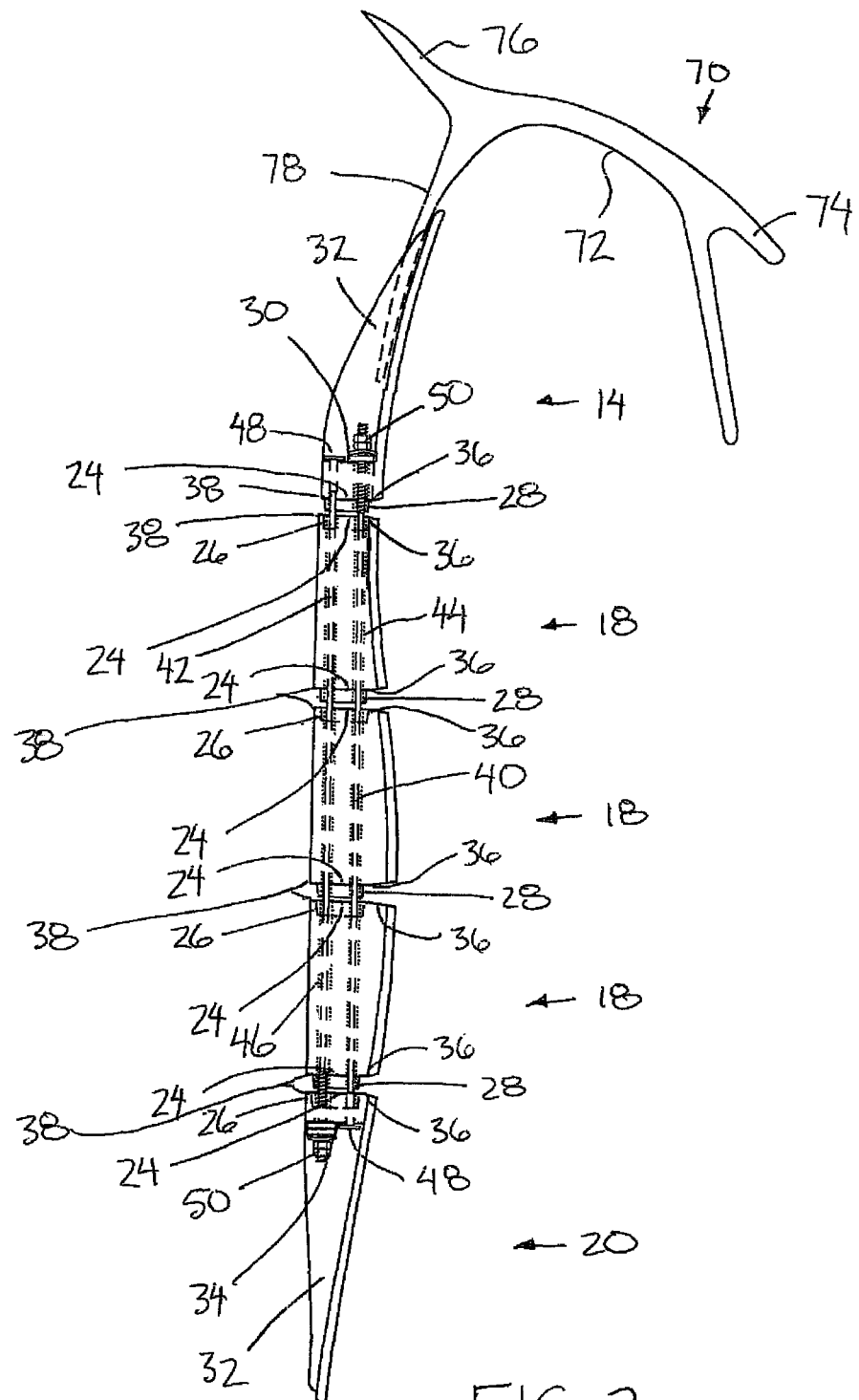
FIG. 2 is an exploded side elevational view of the spinal protective device according to FIG. 1 in combination with a neck protective device.
Figure 3:
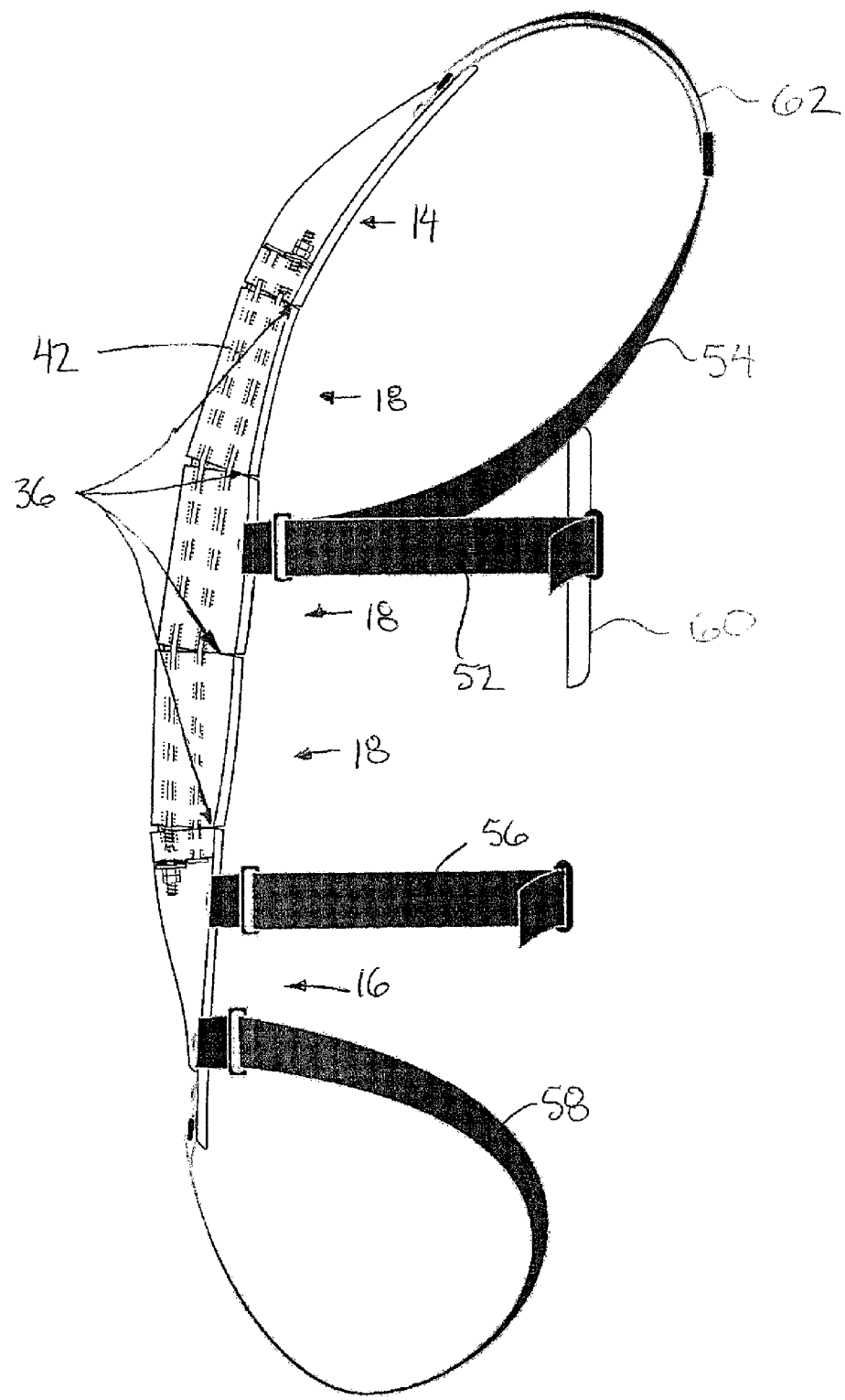
FIG. 3 is a side elevational view of the spinal protective device according to FIG. 1 in which the device is flexed to a hyperflexion limit.
Figure 4:
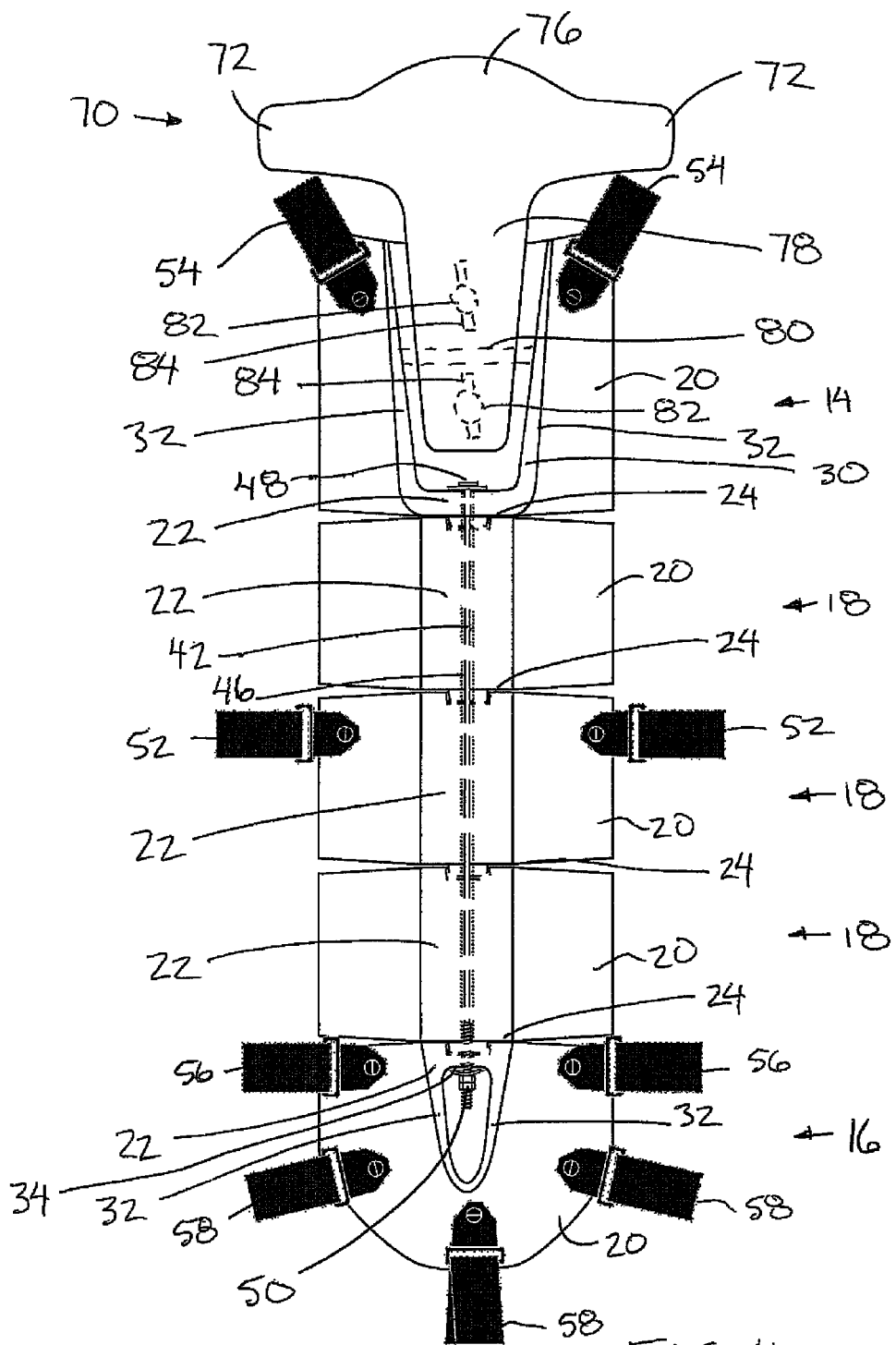
FIG. 4 is a rear elevational view of the spinal protective device according to FIG. 1 in combination with the neck protective device.

The spinal protective device 10 is preferably used in combination with a neck protective device 70. As shown in FIGS. 2 and 4, the neck protective device comprises a separate device arranged to be coupled to the uppermost member 14. In this instance the neck protective device includes a pair of shoulder portions 72 having an inverted U shape for extending over respective shoulders of the user. The front ends of the shoulder portions may be joined across a chest of the user for supporting a forward collar portion 74 extending forwardly from the front ends of the shoulder portions 72 adjacent the top end thereof. The forward collar portion is arranged to be engaged by the front bottom edge of a helmet of the user when the user's head is tilted forwardly beyond a range which is considered safe to prevent neck injury to the user. The rear ends of the shoulder portions are similarly joined by a rear collar portion 76 extending upwardly and rearwardly above the shoulder portions. The rear collar portion 76 is arranged to be engaged by the rear bottom edge of the helmet of the user when the user's head is tilted rearwardly beyond the range of movement which is considered safe to similarly prevent neck injury to the user.

The neck protective device 70 further includes a depending portion 78 extending downwardly from the rear collar portion and shoulder portions at a location laterally centered between the shoulder portions. The uppermost member 14 of the spinal protective device defines a channel at the rear side between the ribs 32 which vertically and slidably receives the depending portion 78 of the neck protective device therein such that the depending portion of the neck protective device overlaps the rear side of the uppermost member 14.

In some embodiments, a strap member 80 spans between the ribs 32 spaced rearwardly from the front panel 20 of the uppermost member 14 to define a pocket that slidably receives the depending portion 78 therein. The strap member serves to retain the depending portion 78 in the channel of the uppermost member for additional support to the neck of the user.

Alternatively a pair of lugs 82 on the uppermost member may be vertically slidable within respective vertical slots 84 in the depending portion to support and retain the depending portion relative to the uppermost member 14 while still allowing some relative vertical sliding movement therebetween.

In the embodiment of FIGS. 2 and 4, the device 10 is designed to be worn in conjunction with available independent neck braces like the Leatt Brace™, the Alpinestars Bionic Neck Support. The addition of a neck support device is critical and necessary in order to provide maximum spinal cord protection. An independent neck support can help transfer the load from an impact to the head into the spinal brace support device. The spinal brace support device will help support the neck support device and will assist in absorbing and distributing the load through its system of retention straps. Also, in the case of sever hyper-extension the load on upper spine at the end of the spinal support device is transferred into the neck support device.

Figure 7:
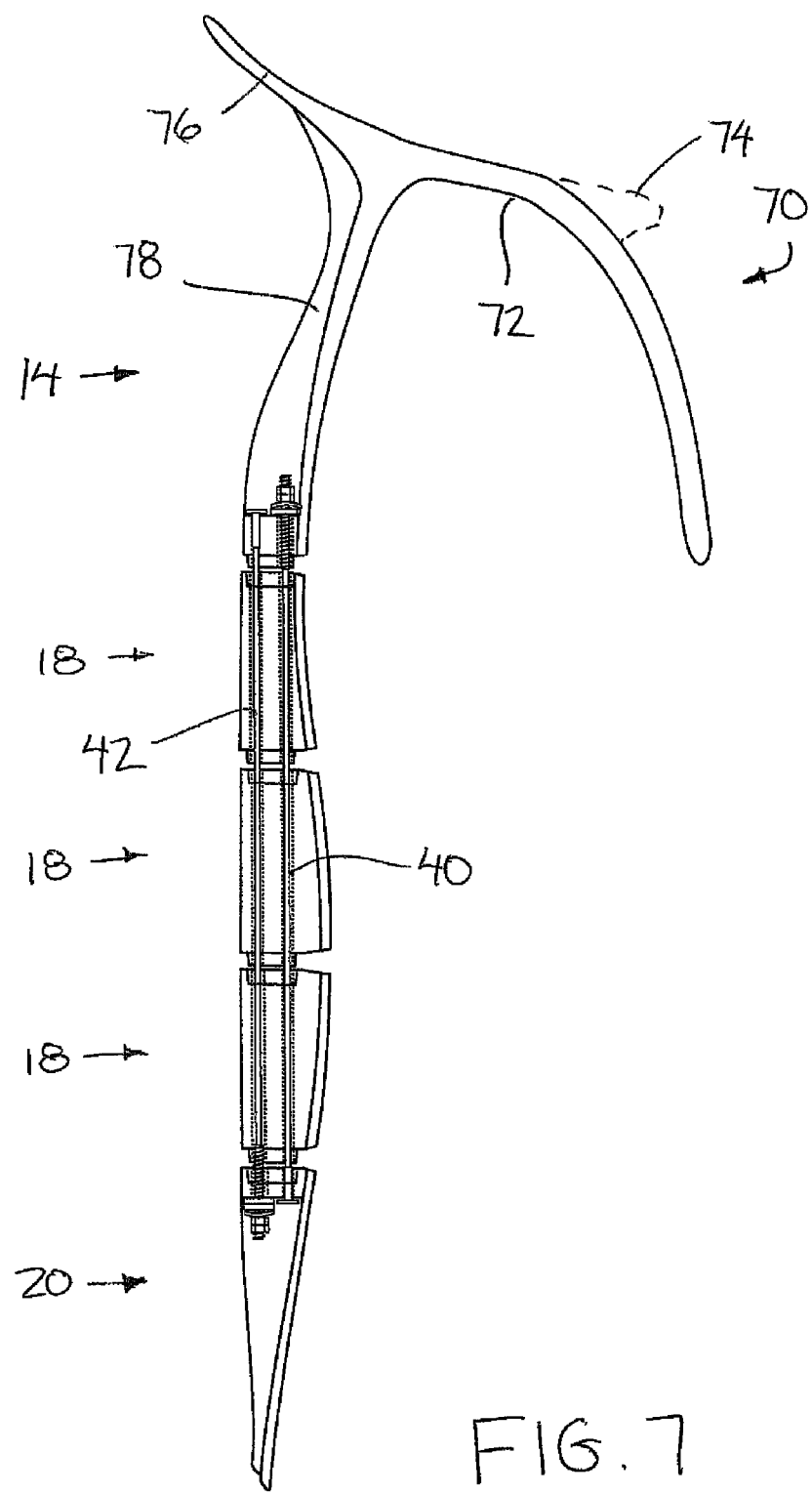
FIG. 7 is a side elevational view of a further embodiment of the uppermost support member including a neck protective device integrally formed therewith.

Alternatively as shown in FIG. 7, the uppermost support member supports the neck protective device 70 integrally therewith. In this instance, the shoulder portions 72, the forward collar portion 74 and the rear collar portion 76 are substantially identical to those described above; however the depending portion 78 is instead integrally formed with the uppermost member 14 of the spinal protective device 10. Accordingly in this instance, the shoulder portions 72, the forward collar portion 74, the rear collar portion 76 and the uppermost member 14 of the spinal protective device comprise a single, continuous, seamless, and integrally formed rigid member securely strapped to the body of the user for optimal spinal and neck support during extreme sports.

The addition of the integrated neck support similarly provides maximum spinal cord protection. The integrated neck support will also transfer the load from an impact to the head into the spinal brace support device and the shoulders of the athlete. Also as noted above, in the case of sever hyper-extension loads to the spine the integrated neck support ensure that the load is transferred into the helmet of the athlete versus the athlete's neck.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A spinal protective device comprising:
   a plurality of support members arranged to be abutted in series with one another in a longitudinal direction so as to extend longitudinally along a spine of a user;

each support member including a supportive inner surface at a front side of the support member which spans in a lateral direction so as to be arranged to extend laterally across a back of the user;

each adjacent pair of support members further comprising a respective pair of forward fulcrum contact areas where the support members abut one another for relative pivotal movement in a hyperflexion direction about a forward lateral axis; and a rear tension member arranged to be connected under tension between the support members at a location spaced rearwardly from the forward fulcrum contact areas so as to be arranged to limit relative movement between the support members in the hyperflexion direction; and a plurality of straps arranged to be extended about a torso of a user so as to secure the support members extending longitudinally along the spine of the user;

wherein the support members include an uppermost support member at a top end, a lowermost support member at a bottom end and at least one intermediate support member between the uppermost and lowermost support members, the rear tension member being anchored at opposing ends on the uppermost and lowermost support members respectively and extending through said at least one intermediate support member.

2. The device according to claim 1 wherein the rear tension member comprises a single, integral and flexible member spanning all of the support members and which is adjustable in tension.

3. The device according to claim 1 wherein each support member comprises a forward portion generally comprising a plate spanning in the lateral direction to define the inner surface arranged to engage the user and a rearward portion comprising a lobe projecting rearwardly outwardly from the forward portion at a central location thereon and which defines the fulcrum contact areas thereon.

4. The device according to claim 1 wherein the inner surfaces of adjacent support members are supported relative to the fulcrum contact areas so as to be arranged to remain spaced apart from one another in the longitudinal direction when the support members are pivoted relative to one another in the hyperflexion direction to a hyperflexion limit prescribed by the rear tension member.

5. The device according to claim 1 wherein the forward fulcrum contact areas are spaced rearwardly from the inner surfaces of the respective support members.

6. The device according to claim 1 wherein each support member of each adjacent pair of support members includes an end face oriented transversely to the rear tension member in abutment with the end face of the other support member of the adjacent pair of support members, the end faces locating the forward fulcrum contact areas thereon.

7. The device according to claim 1 further comprising a pair of shoulder portions integrally formed with an uppermost one of the support members which are arranged to extend over respective shoulders of the user and a rear collar portion integrally formed with the uppermost one of the support members to extend upwardly therefrom above the shoulder portions so as to be arranged to limit rearward movement of a head of the user.

8. A spinal protective device comprising:

a plurality of support members arranged to be abutted in series with one another in a longitudinal direction so as to extend longitudinally along a spine of a user;

each support member including a supportive inner surface at a front side of the support member which spans in a lateral direction so as to be arranged to extend laterally across a back of the user;

each adjacent pair of support members further comprising a respective pair of forward fulcrum contact areas where the support members abut one another for relative pivotal movement in a hyperflexion direction about a forward lateral axis; and a rear tension member arranged to be connected under tension between the support members at a location spaced rearwardly from the forward fulcrum contact areas so as to be arranged to limit relative movement between the support members in the hyperflexion direction; and a plurality of straps arranged to be extended about a torso of a user so as to secure the support members extending longitudinally along the spine of the user;

wherein the rear tension member is received through respective bores extending in the longitudinal direction through respective ones of the support members, the bores being elongate in the lateral direction.

9. A spinal protective device comprising:

a plurality of support members arranged to be abutted in series with one another in a longitudinal direction so as to extend longitudinally along a spine of a user;

each support member including a supportive inner surface at a front side of the support member which spans in a lateral direction so as to be arranged to extend laterally across a back of the user;

each adjacent pair of support members further comprising a respective pair of forward fulcrum contact areas where the support members abut one another for relative pivotal movement in a hyperflexion direction about a forward lateral axis; and a rear tension member arranged to be connected under tension between the support members at a location spaced rearwardly from the forward fulcrum contact areas so as to be arranged to limit relative movement between the support members in the hyperflexion direction; and a plurality of straps arranged to be extended about a torso of a user so as to secure the support members extending longitudinally along the spine of the user;

wherein each adjacent pair of support members further comprises a respective pair of rearward fulcrum contact areas where the support members abut one another for relative pivotal movement in a hyperextension direction about a rearward lateral axis and wherein there is provided a front tension member arranged to be connected under tension between the support members at a location spaced forwardly from the rearward fulcrum contact areas so as to be arranged to limit relative movement between the support members in the hyperextension direction.

10. The device according to claim 9 wherein the front tension member and the rear tension member are independently adjustable in length.

11. The device according to claim 9 wherein the forward fulcrum contact areas are spaced forwardly towards the inner surfaces of the support members in relation to the corresponding rearward fulcrum contact areas.

12. The device according to claim 11 wherein the tension members are located between the forward and rearward fulcrum contact areas.

13. The device according to claim 9 wherein the fulcrum contact areas and the tension members are aligned in a generally common vertical plane oriented perpendicularly to the lateral direction.

14. The device according to claim 9 wherein the support members are only connected by the abutment of respective ends with one another and the tension members connected between the support members.

15. The device according to claim 9 wherein one of the support members of each adjacent pair comprises a protrusion and the other one of the support members of the adjacent pair comprises a socket arranged to receive the protrusion therein between the respective forward and rearward fulcrum contact areas of the support members.

16. The device according to claim 15 wherein the protrusion is arranged to mate with the socket such that the respective support members are pivotal relative to one another about a longitudinally extending axis within a prescribed range.

17. A spinal protective device comprising:
   a plurality of support members arranged to be abutted in series with one another in a longitudinal direction so as to extend longitudinally along a spine of a user;
   each support member including a supportive inner surface at a front side of the support member which spans in a lateral direction so as to be arranged to extend laterally across a back of the user;
   each adjacent pair of support members further comprising a respective pair of forward fulcrum contact areas where the support members abut one another for relative pivotal movement in a hyperflexion direction about a forward lateral axis; and
   a rear tension member arranged to be connected under tension between the support members at a location spaced rearwardly from the forward fulcrum contact areas so as to be arranged to limit relative movement between the support members in the hyperflexion direction; and
   a plurality of straps arranged to be extended about a torso of a user so as to secure the support members extending longitudinally along the spine of the user;
   wherein each adjacent pair of support members abuts one another at respective ends faces and each end face further comprises a first lateral fulcrum and a second lateral fulcrum spaced apart in laterally opposed directions from the rear tension member, each adjacent pair of support members being arranged to abut one another at the first lateral fulcrums respectively for relative pivotal movement in a first lateral direction up to a first lateral limit when the rear tension member is under tension, and each adjacent pair of support members being arranged to abut one another at the second lateral fulcrums respectively for relative pivotal movement in a second lateral direction up to a second lateral limit when the rear tension member is under tension.

18. The device according to claim 17 wherein each adjacent pair of support members further comprises a respective pair of rearward fulcrum contact areas where the support members abut one another for relative pivotal movement in a hyperextension direction about a rearward lateral axis and wherein there is provided a front tension member arranged to be connected under tension between the support members at a location spaced forwardly from the rearward fulcrum contact areas so as to be arranged to limit relative movement between the support members in the hyperextension direction, and wherein the first and second lateral fulcrums are substantially centered between the front and rear tensions members in a direction of a transverse axis extending between the front and rear tensions members.

19. A spinal protective device in combination with neck protective device, the spinal protective device comprising:
   a plurality of support members arranged to be abutted in series with one another in a longitudinal direction so as to extend longitudinally along a spine of a user;
   each support member including a supportive inner surface at a front side of the support member which spans in a lateral direction so as to be arranged to extend laterally across a back of the user;
   each adjacent pair of support members further comprising a respective pair of forward fulcrum contact areas where the support members abut one another for relative pivotal movement in a hyperflexion direction about a forward lateral axis; and
   a rear tension member arranged to be connected under tension between the support members at a location spaced rearwardly from the forward fulcrum contact areas so as to be arranged to limit relative movement between the support members in the hyperflexion direction; and
   a plurality of straps arranged to be extended about a torso of a user so as to secure the support members extending longitudinally along the spine of the user;
   wherein the neck protective device comprises a pair of shoulder portions arranged to extend over respective shoulders of a user, a rear collar portion joined between the shoulder portions to extend upwardly therefrom so as to be arranged to limit rearward movement of a head of the user, and a depending portion arranged to extending downwardly from the rear collar portion along a back of the user; and
   wherein an uppermost one of the support members includes a channel at a rear side of the support member arranged to receive the depending portion of the neck protective device therein.

* * * * *